United States Patent
Howard et al.

(10) Patent No.: US 10,981,011 B2
(45) Date of Patent: *Apr. 20, 2021

(54) ELECTRICAL STIMULATION SYSTEM WITH INTRAOPERATIVE CABLE AND METHODS OF MAKING AND USING

(71) Applicant: Boston Scientific Neuromodulation Corporation, Valencia, CA (US)

(72) Inventors: Joshua Dale Howard, Sacramento, CA (US); Christopher Shanahan, Santa Rosa, CA (US); Geoffrey Abellana Villarta, Valencia, CA (US); Peter J. Yoo, Burbank, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 117 days.

This patent is subject to a terminal disclaimer.

(21) Appl. No.: 16/216,703

(22) Filed: Dec. 11, 2018

(65) Prior Publication Data

US 2019/0105501 A1    Apr. 11, 2019

Related U.S. Application Data

(63) Continuation of application No. 14/992,931, filed on Jan. 11, 2016, now Pat. No. 10,195,446.

(Continued)

(51) Int. Cl.
*A61N 1/372* (2006.01)
*A61N 1/05* (2006.01)
(Continued)

(52) U.S. Cl.
CPC .......... *A61N 1/37241* (2013.01); *A61N 1/05* (2013.01); *H01R 4/28* (2013.01); *A61N 1/0551* (2013.01); *A61N 1/0595* (2013.01); *A61N 1/3752* (2013.01)

(58) Field of Classification Search
CPC ............... A61N 1/3752; A61N 1/0551; A61N 1/37241; A61N 1/0595; A61N 1/05; H01R 4/28

See application file for complete search history.

(56) References Cited

U.S. PATENT DOCUMENTS 5,354,326 A    10/1994    Comben et al.
5,782,892 A     7/1998    Castle et al.
(Continued)

FOREIGN PATENT DOCUMENTS

EP          2535009         12/2012
WO       2012/075497        6/2012

OTHER PUBLICATIONS

U.S. Appl. No. 14/962,938, filed Dec. 8, 2015.
(Continued)

*Primary Examiner* — Tammie K Marlen
(74) *Attorney, Agent, or Firm* — Branch Partners PLLC; Bruce E. Black

(57) ABSTRACT

An operating room cable assembly for electrically coupling at least one implantable electrical stimulation lead to a trial stimulator includes an elongated body; a trial stimulator connector disposed at one end of the elongated body; and a lead connector disposed at another end of the elongated body. The lead connector can include one or more buttons that can be pushed to load a lead into the lead connector and released to retain the lead. Alternatively, the lead connector can include a lever that can be operated to load the lead. A further alternative is a slider with a lead engagement element that can be slid between positions allowing loading of a lead and engagement of the lead. Other alternatives include a lead connector with doors that can swing open to allow loading of a lead or a collet/sleeve that can be tightened on the lead.

20 Claims, 10 Drawing Sheets

Related U.S. Application Data

(60) Provisional application No. 62/104,497, filed on Jan. 16, 2015.

(51) Int. Cl.
*H01R 4/28* (2006.01)
*A61N 1/375* (2006.01)

(56) References Cited

U.S. PATENT DOCUMENTS

| | | | |
|---|---|---|---|
| 5,931,861 A | 8/1999 | Werner et al. | |
| 6,038,479 A | 3/2000 | Werner et al. | |
| 6,038,481 A | 3/2000 | Werner et al. | |
| 6,181,969 B1 | 1/2001 | Gord | |
| 6,192,278 B1 | 2/2001 | Werner et al. | |
| 6,343,233 B1 | 1/2002 | Werner et al. | |
| 6,397,108 B1 | 5/2002 | Camps et al. | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,687,538 B1 | 2/2004 | Hrdlicka et al. | |
| 6,741,892 B1 | 8/2004 | Meadows et al. | |
| 6,950,709 B2 | 9/2005 | Baudino | |
| 6,980,863 B2 | 12/2005 | van Venrooij et al. | |
| 7,244,150 B1 | 7/2007 | Brase et al. | |
| 7,437,193 B2 | 10/2008 | Parramon et al. | |
| 7,493,159 B2 | 2/2009 | Hrdlicka et al. | |
| 7,539,542 B1 | 5/2009 | Malinowski | |
| 7,548,788 B2 | 6/2009 | Chinn et al. | |
| 7,563,141 B2 | 7/2009 | Alexander et al. | |
| 7,594,828 B2 | 9/2009 | Alexander et al. | |
| 7,633,023 B1 | 12/2009 | Cappa et al. | |
| 7,672,734 B2 | 3/2010 | Anderson et al. | |
| 7,736,192 B2 | 6/2010 | Alexander et al. | |
| 7,761,165 B1 | 7/2010 | He et al. | |
| 7,949,395 B2 | 5/2011 | Kuzma | |
| 7,974,706 B2 | 7/2011 | Moffitt et al. | |
| 8,175,710 B2 | 5/2012 | He | |
| 8,224,450 B2 | 7/2012 | Brase | |
| 8,239,042 B2 | 8/2012 | Chinnn et al. | |
| 8,364,278 B2 | 1/2013 | Pianca et al. | |
| 8,401,670 B2 | 3/2013 | Mehdizadeh et al. | |
| 8,849,396 B2 | 9/2014 | DeRohan et al. | |
| 9,101,775 B2 | 8/2015 | Barker | |
| 2003/0199948 A1 | 10/2003 | Kokones et al. | |
| 2004/0106964 A1 | 6/2004 | Fischer, Sr. et al. | |
| 2005/0165465 A1 | 7/2005 | Pianca et al. | |
| 2007/0150036 A1 | 6/2007 | Anderson | |
| 2007/0197896 A1 | 8/2007 | Moll et al. | |
| 2010/0070012 A1 | 3/2010 | Chinn et al. | |
| 2010/0106204 A1 | 4/2010 | Moffitt et al. | |
| 2010/0249869 A1 | 9/2010 | Ries et al. | |
| 2011/0082532 A1 | 4/2011 | Khursenko | |
| 2011/0098795 A1 | 4/2011 | Mehdizadeh et al. | |
| 2011/0207352 A1 | 8/2011 | Camps et al. | |
| 2011/0218549 A1 | 9/2011 | Barker | |
| 2011/0257503 A1 | 10/2011 | Mehdizadeh et al. | |
| 2013/0098678 A1 | 4/2013 | Barker | |
| 2015/0025609 A1 | 1/2015 | Govea | |

OTHER PUBLICATIONS

Partial International Search Report for PCT Application No. PCT/US2016/012892 dated May 31, 2016.

International Search Report and Written Opinion for PCT Application No. PCT/US2016/012892 dated Aug. 22, 2016.

Official Communication for U.S. Appl. No. 14/992,931 dated Oct. 27, 2017.

Official Communication for U.S. Appl. No. 14/992,931 dated Jan. 9, 2018.

ELECTRICAL STIMULATION SYSTEM WITH INTRAOPERATIVE CABLE AND METHODS OF MAKING AND USING

CROSS-REFERENCE TO RELATED APPLICATIONS

This application is a continuation of U.S. patent application Ser. No. 14/992,931, filed Jan. 11, 2016, which issued as U.S. Pat. No. 10,195,446, which claims the benefit under 35 U.S.C. § 119(e) of U.S. Provisional Patent Application Ser. No. 62/104,497, filed Jan. 16, 2015, both of which are incorporated herein by reference.

FIELD

The present invention is directed to the area of implantable electrical stimulation systems and methods of making and using the systems. The present invention is also directed implantable electrical stimulation systems having an operating room cable with a lead locking mechanism, as well as methods of making and using the cable and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an operating room cable assembly for electrically coupling at least one implantable electrical stimulation lead to a trial stimulator. The operating room cable assembly includes an elongated body having a first end portion and an opposing second end portion; a trial stimulator connector disposed along the second end portion of the elongated body; and a lead connector disposed along the first end portion of the elongated body and electrically coupled to the trial stimulator connector. The lead connector mechanically receives a proximal end portion of at least one electrical stimulation lead or lead extension. The lead connector includes a connector body, at least one lead channel defined within the connector body to receive a portion of the at least one electrical stimulation lead or lead extension, at least one button with each button defining at least one button lead channel to receive a portion of the at least one electrical stimulation lead or lead extension, at least one spring disposed within the connector body and biasing the at least one button outwards from the connector body, and connector contacts disposed within the connector body and arranged along the at least one lead channel to make electrical contact with terminals disposed on the at least one electrical stimulation lead or lead extension when the at least one electrical stimulation lead or lead extension is received in the at least one lead channel. The at least one spring biases the at least one button so that the at least one button lead channel is misaligned with the at least one lead channel and so that the at least one button can be pushed to align at least one of the at least one button lead channel with one of the at least one lead channel so that a portion of one of the at least one electrical stimulation lead or lead extension can be received therein and so that when the at least one button is released the at least one spring biases the at least one button outward to hold the at least one electrical stimulation lead or lead extension within the lead connector.

In at least some embodiments, the at least one button is a single button. In at least some embodiments, the at least one button is two buttons, the at least one lead channel is two lead channels, the at least one spring is two springs, and each button is associated with one of the lead channels and one of the springs.

In at least some embodiments, the lead connector further defines a side-loading lead aperture associated with each of the at least one lead channel and sufficiently sized so that the portion of the at least one electrical stimulation lead or lead extension can be laterally loaded into the at least one lead channel. In at least some embodiments, the lead connector further defines a side-loading stylet aperture associated with each of the at least one lead channel and sufficiently sized so that a portion of a stylet disposed in the at least one electrical stimulation lead or lead extension can be laterally loaded into the at least one lead channel.

In at least some embodiments, the connector body further defines a recess and the at least one button includes a protrusion disposed within the recess, wherein the recess and protrusion are configured and arranged to limit upward or downward movement of the at least one button. In at least some embodiments, each button includes at least one lead retention elements associated with each button lead channel to facilitate retention of the lead within the button lead channel.

Another embodiment is an operating room cable assembly for electrically coupling at least one implantable electrical stimulation lead to a trial stimulator. The operating room cable assembly includes an elongated body having a first end portion and an opposing second end portion; a trial stimulator connector disposed along the second end portion of the elongated body; and a lead connector disposed along the first end portion of the elongated body and electrically coupled to the trial stimulator connector. The lead connector mechanically receives a proximal end portion of at least one electrical stimulation lead or lead extension. The lead connector includes a connector body defining a slider aperture, at least one lead channel defined within the connector body to receive a portion of the at least one electrical stimulation lead or lead extension, rails disposed within the connector body with each of the rails defining a track so that a distance between the track and a one of the at least one lead channel increases from a first end of the connector body to a second end of the connector body, a slider to slide along the slider aperture, at least one lead engagement element coupled to the slider to travel along the track and to engage the at least one electrical stimulation lead or lead extension when the slider is at or near the first end of the connector body, and connector contacts disposed within the connector body and arranged along the at least one lead channel to make electrical contact with terminals disposed on the at least one electrical stimulation lead or lead extension when the at least one electrical stimulation lead or lead extension is received in the at least one lead channel. Each connector contact is a plate that is deformed when the lead engagement element engages the at least one electrical stimulation lead or lead extension.

A further embodiment is an operating room cable assembly for electrically coupling at least one implantable electrical stimulation lead to a trial stimulator. The operating room cable assembly includes an elongated body having a first end portion and an opposing second end portion; a trial stimulator connector disposed along the second end portion of the elongated body; and a lead connector disposed along the first end portion of the elongated body and electrically coupled to the trial stimulator connector. The lead connector mechanically receives a proximal end portion of at least one electrical stimulation lead or lead extension. The lead connector includes a connector body, at least one lead channel defined within the connector body to receive a portion of the at least one electrical stimulation lead or lead extension, a lever, at least one lead engagement element disposed at one end of the lever to engage the at least one electrical stimulation lead or lead extension unless a user operates the lever to lift the at least one lead engagement element away from the at least one lead channel, and connector contacts disposed within the connector body and arranged along the at least one lead channel to make electrical contact with terminals disposed on the at least one electrical stimulation lead or lead extension when the at least one electrical stimulation lead or lead extension is received in the at least one lead channel.

In at least some embodiments, the lead connector further includes at least one spring disposed within the connector body and biasing the at least one lever to maintain the at least one engagement element in contact with the at least one electrical stimulation lead or lead extension when the at least one electrical stimulation lead or lead extension is disposed in the at least one lead channel.

Yet another embodiment is an operating room cable assembly for electrically coupling at least one implantable electrical stimulation lead to a trial stimulator. The operating room cable assembly includes an elongated body having a first end portion and an opposing second end portion; a trial stimulator connector disposed along the second end portion of the elongated body; and a lead connector disposed along the first end portion of the elongated body and electrically coupled to the trial stimulator connector. The lead connector mechanically receives a proximal end portion of at least one electrical stimulation lead or lead extension. The lead connector includes a connector body, at least one lead channel defined within the connector body and configured and arranged to receive a portion of the at least one electrical stimulation lead or lead extension, at least one door coupled to the connector body to swing between a closed position and an open position with each door defining a door channel that lies opposite a portion of a one of the at least one lead channel when the door is in the closed position, and connector contacts disposed within the connector body and arranged along the at least one lead channel to make electrical contact with terminals disposed on the at least one electrical stimulation lead or lead extension when the at least one electrical stimulation lead or lead extension is received in the at least one lead channel. The door is configured and arranged to hold a lead disposed within the lead channel and door channel when the door is in the closed position.

In at least some embodiments, the operating room cable assembly also includes a slider coupled to the connector body to slide onto a portion of each door to retain the door in the closed position.

A further embodiment is an operating room cable assembly for electrically coupling at least one implantable electrical stimulation lead to a trial stimulator. The operating room cable assembly includes an elongated body having a first end portion and an opposing second end portion; a trial stimulator connector disposed along the second end portion of the elongated body; and a lead connector disposed along the first end portion of the elongated body and electrically coupled to the trial stimulator connector. The lead connector mechanically receives a proximal end portion of at least one electrical stimulation lead or lead extension. The lead connector includes a connector body, at least one lead channel defined within the connector body and configured and arranged to receive a portion of the at least one electrical stimulation lead or lead extension, at least one lead retainer coupled to the connector body and associated with a one of the at least one lead channel, and connector contacts disposed within the connector body and arranged along the at least one lead channel to make electrical contact with terminals disposed on the at least one electrical stimulation lead or lead extension when the at least one electrical stimulation lead or lead extension is received in the at least one lead channel. Each lead retainer includes a collet and a sleeve disposed around the collet. The sleeve and collet are configured and arranged to increase or decrease an inner diameter of the collet using the sleeve. The lead connector is configured and arranged to receive a portion of at least one electrical stimulation lead or lead extension through the at least one lead retainer and into the at least one lead channel and the at least one lead retainer is configured and arranged to be tightened around the at least one electrical stimulation lead or lead extension for retention In at least some embodiments, the sleeve and collet are configured and arranged to increase or decrease an inner diameter of the collet by rotating the sleeve.

Yet another embodiment is a kit including any of the operating room cable assemblies described above and at least one electrical stimulation lead. The kit can also include a lead extension. Another embodiment is a kit including any of the operating room cable assemblies described above and at least one lead extension.

A further embodiment is a trial stimulation arrangement for an electrical stimulation system that includes any of the kits described above and a trial stimulator configured and arranged to generate electrical stimulation signals, the trial stimulator disposed external to a patient and coupleable to the trial stimulator connector of the operating room cable assembly of the kit.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed implantable electrical stimulation systems having an operating room cable with a lead locking mechanism, as well as methods of making and using the cable and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
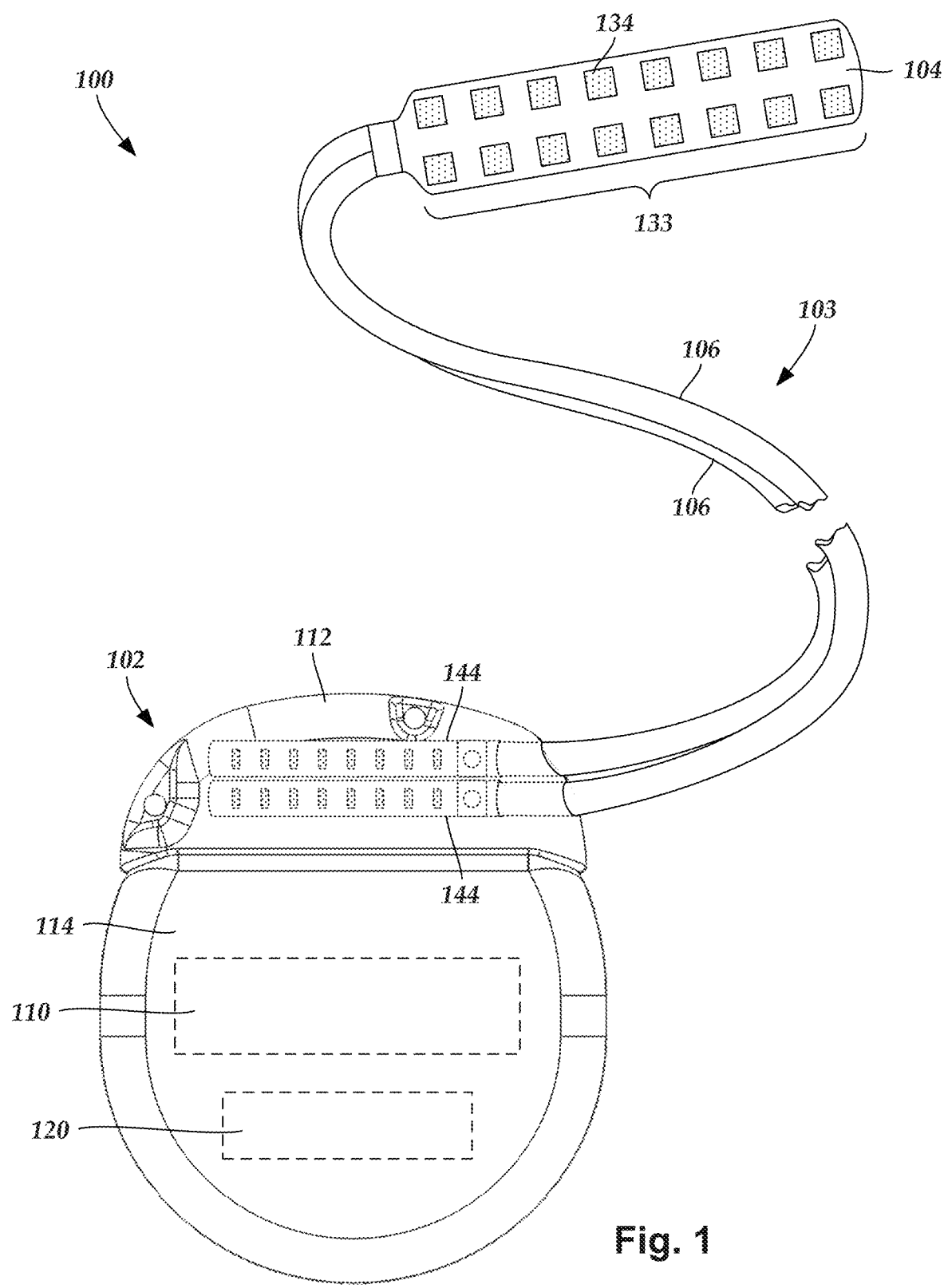
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (e.g., 310 in FIG. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
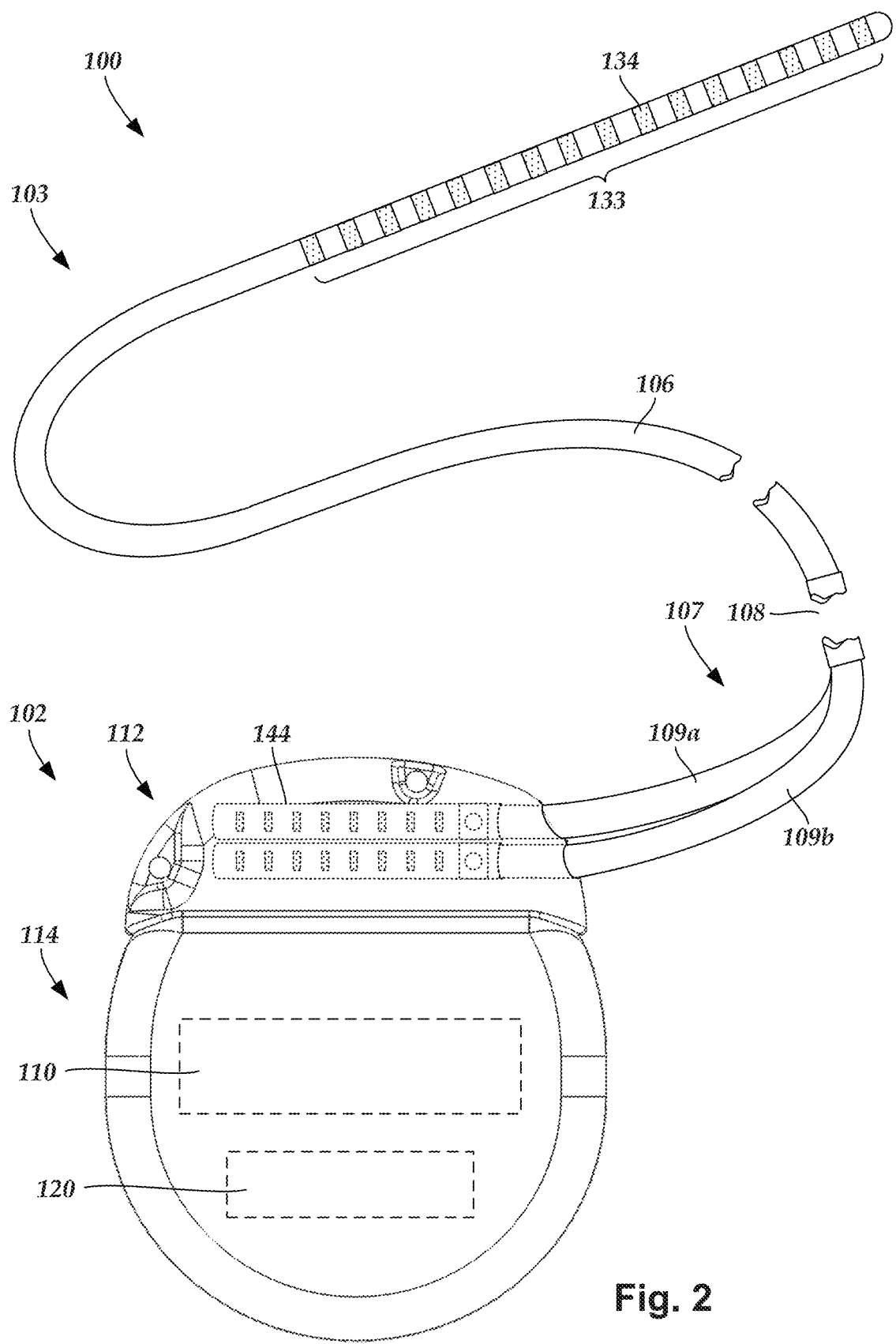
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
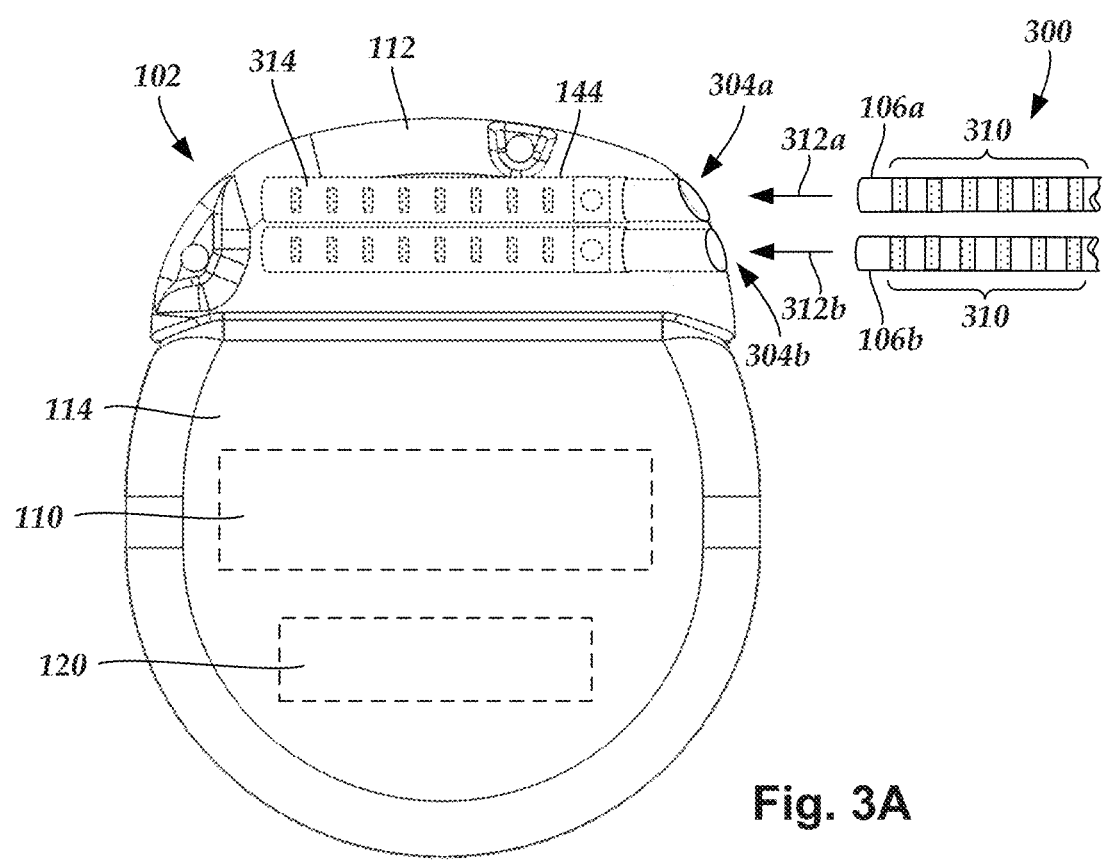
FIG. 3A is a schematic view of one embodiment of the control module of FIG. 1 configured and arranged to electrically couple to an elongated device, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIG. 3A). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
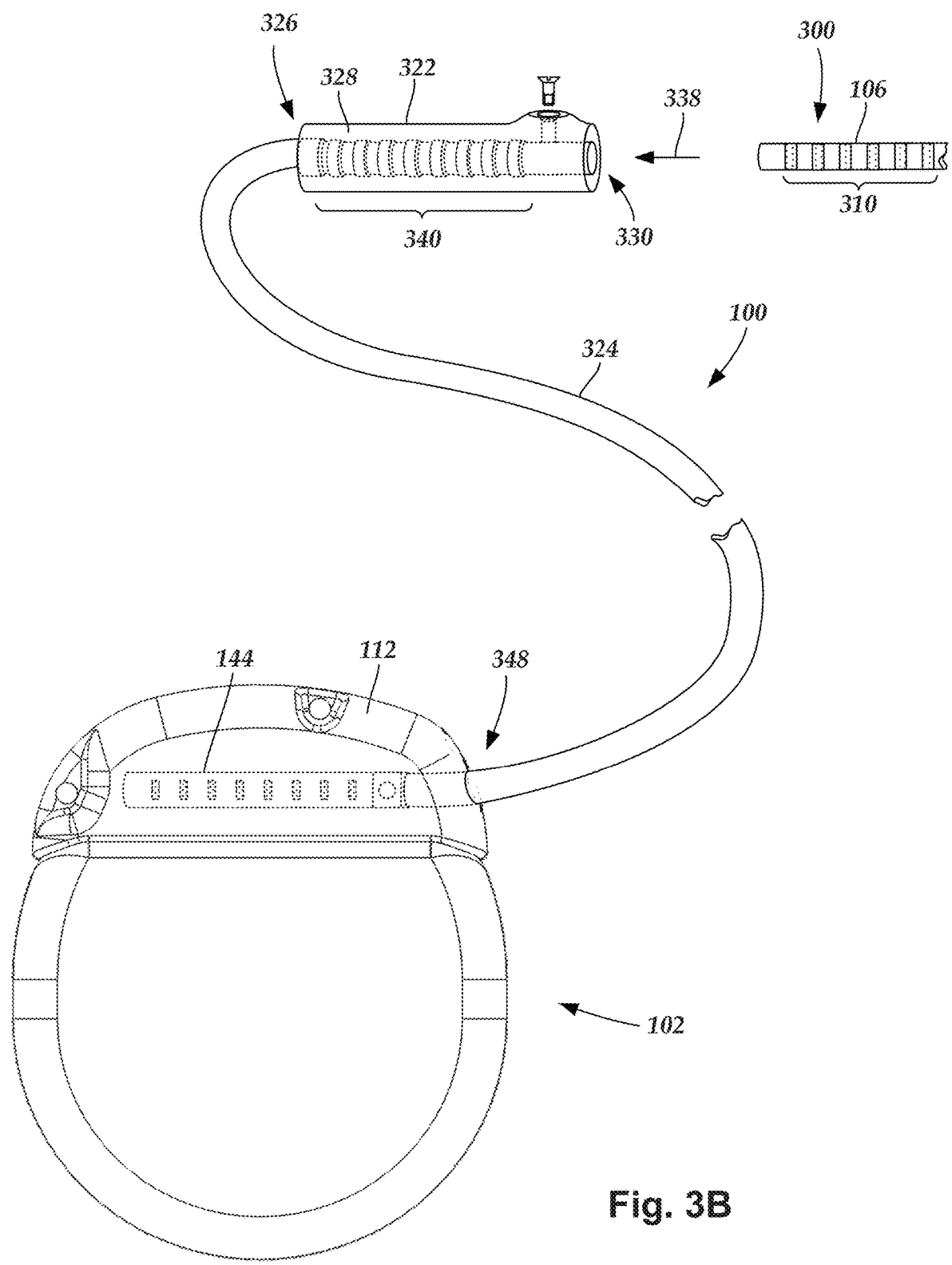
FIG. 3B is a schematic view of one embodiment of a lead extension configured and arranged to electrically couple the elongated device of FIG. 2 to the control module of FIG. 1, according to the invention.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Figure 4:
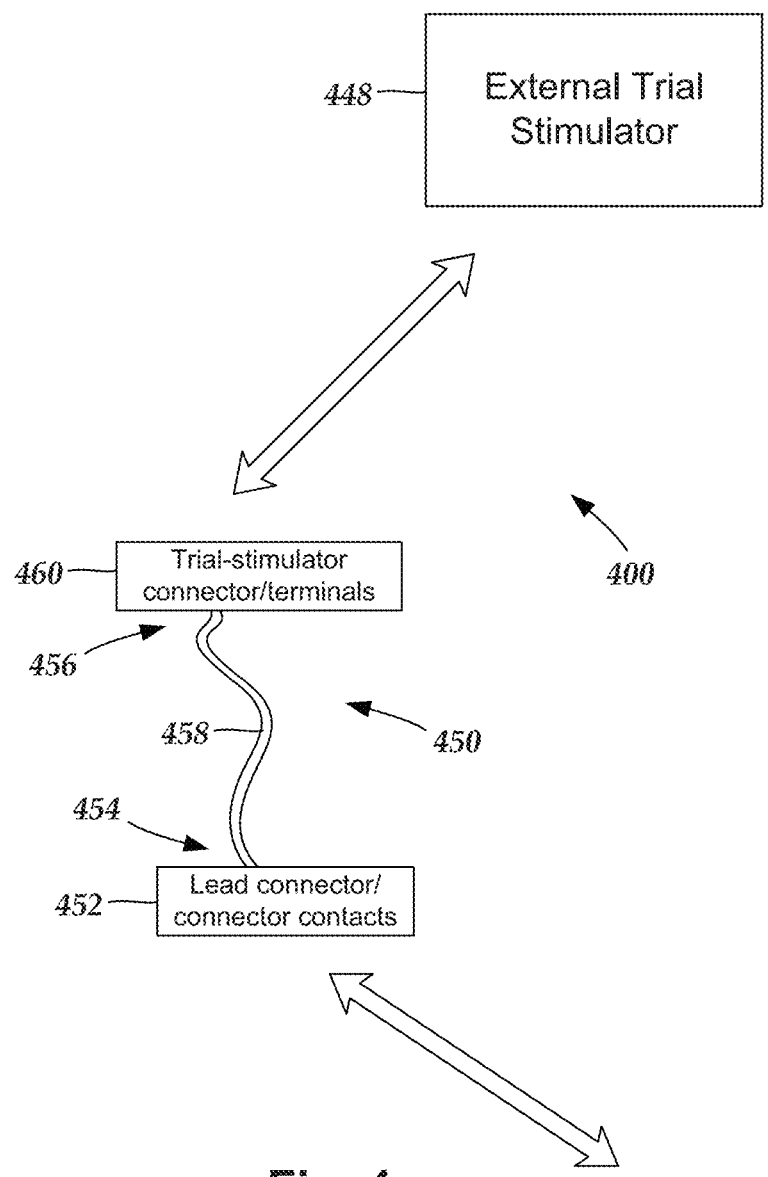
FIG. 4 is a schematic illustration of components of one embodiment of a trial stimulation system, according to the invention.

Turning to FIG. 4, during implantation of the lead into a patient it is sometimes desirable to test the positioning or functionality of the electrodes within the patient prior to completion of the implantation. One way to test electrode positioning or functionality is to implant an electrode-including distal end portion of a lead (and, optionally, one or more lead extensions) into the patient. The proximal end portion of the lead (or lead extension) can then be electrically coupled to a trial stimulator that is disposed external to the patient to perform trial stimulations using the electrodes. Once it is determined that the electrodes are properly positioned and functioning within desired parameters, the trial stimulator can be removed from the proximal end portion of the lead (or lead extension) and replaced with an implantable control module, and the implantation can be completed.

In some embodiments, the trial stimulations can continue for two, four, six, eight, twelve, or more hours or for one, two, three, four, five or more days. In these instances, the patient may be in a hospital or other care facility. In some embodiments, the trial stimulations may continue for an extended period (e.g., 2-10 days or more) where the patient is sent home with the lead, cable, and trial stimulator to assess the effectiveness of the therapy to determine if a permanent implanted system will be effective in treating the medical condition. During the trial stimulations, the lead can be electrically coupled to the trial stimulator by electrically coupling the proximal end portion of the lead (or lead extension) to an operating room cable ("cable") which, in turn, is electrically coupled to the trial stimulator. In some cases, when multiple leads are implanted into a patient, multiple leads (or lead extensions) may be coupled to the cable.

FIG. 4 is a schematic view of one embodiment of a trial stimulation arrangement 400 that includes a lead 403, a trial stimulator 448, and an operating room cable assembly 450, that couples the lead 403 to the trial stimulator 448. The lead 403 includes an array of electrodes 434 and an array of terminals 410. The terminals 410 are configured and arranged to couple the electrodes 434 to the trial stimulator 448 when the operating room cable assembly 450 is coupled to each of the lead 403 and the trial stimulator 448.

During operation, the electrodes 434 are disposed internal to the patient, while the terminals 410 remain external to the patient, as shown in FIG. 4 by a line 462 schematically representing patient skin. Optionally, the trial stimulation arrangement 400 includes one or more additional devices (e.g., a lead extension, an operating room cable extension, a splitter, an adaptor, or the like or any combination thereof).

The operating room cable assembly 450 includes an elongated body 458 having a first end portion 454 and an opposing second end portion 456, a lead connector 452 with connector contacts, and a trial stimulator connector 460 optionally with terminals (terminals are not needed if the trial stimulator connector is permanently wired to the trial stimulator). Conductors (not shown) extend from the connector contacts of the lead connector to the terminals of the trial stimulator connector. The lead connector 452 is disposed along the first end portion 454 of the operating room cable assembly 450 and the connector contacts within the lead connector are coupleable to the terminals 434 of the lead 403 (or lead extension). The trial stimulator connector 460 is disposed along the second end portion 456 of the operating room cable assembly 450 and is coupleable to the trial stimulator 448, either directly or via one or more operating room cable extensions. Any suitable connector contacts and terminals can be used in the operating room cable assembly including rings, c-shaped contacts, plate contacts, pogo pins, and the like. Examples of connector contacts and terminals can be found in, for example, U.S. Pat. Nos. 7,539,542 and 8,849,396; U.S. Patent Application Publication No. 2013/0098678; and U.S. patent application Ser. No. 14/330,330, all of which are incorporated herein by reference.

Conventionally, the lead connectors of the operating room cable assembly are relatively large, bulky, and heavy. In some instances, conventional lead connectors may require two hands to operate. In some instances, it may not be clear to surgical personnel how to load a lead into the lead connector or how to "lock" the lead within the lead connector.

In the description below, leads will be referred to in connection with the lead connector. It will be understood, however, that a lead extension can be used in place of any of the leads.

Figure 5A:
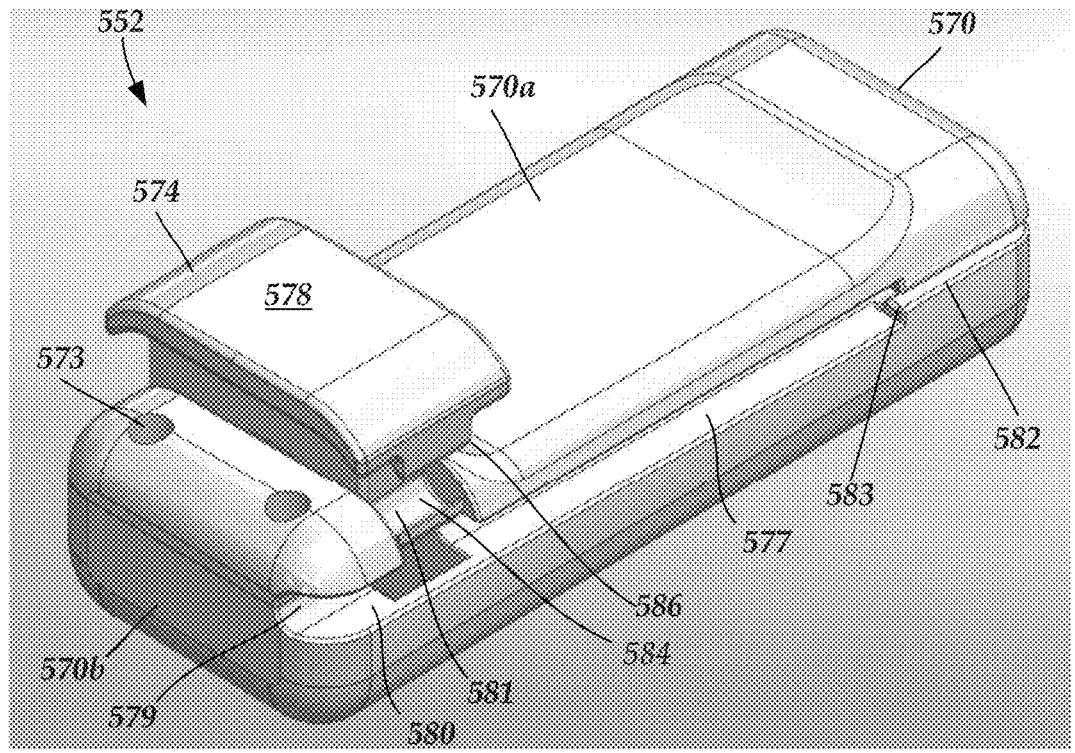
FIG. 5A is a schematic perspective view of one embodiment of a lead connector of an operating room cable assembly, according to the invention.
Figure 5B:
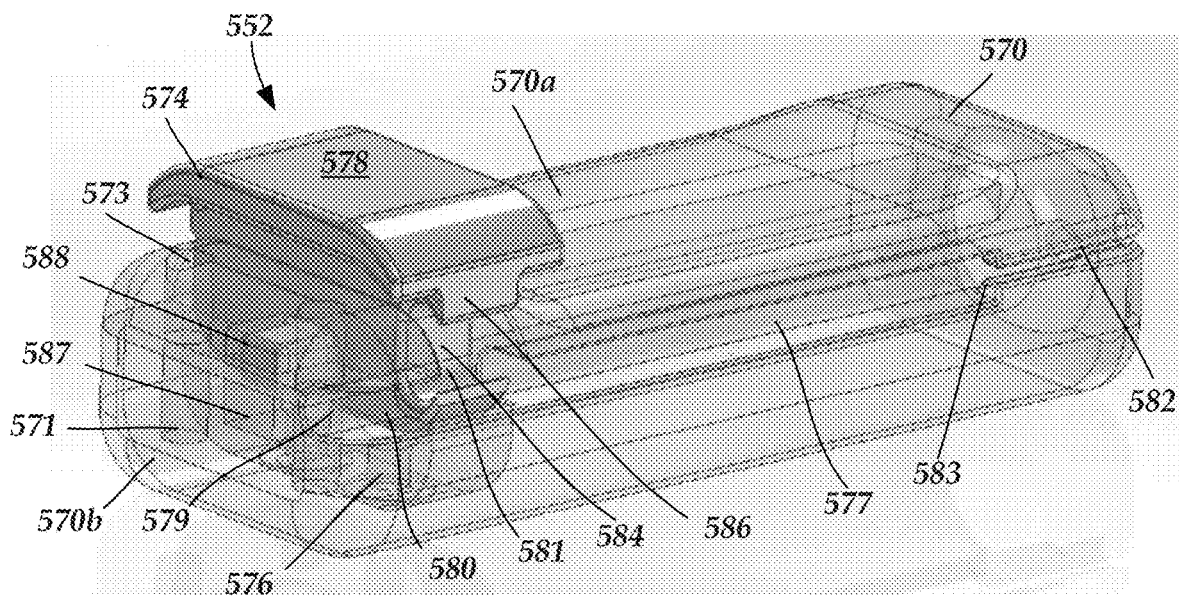
FIG. 5B is a schematic perspective view of the lead connector of FIG. 5A with the body made transparent for illustration purposes, according to the invention.

FIGS. 5A and 5B illustrate one embodiment of a lead connector 552 of an operating room cable assembly (such as operating room cable assembly 450 of FIG. 4) with an elongated body (not shown) extending from the lead connector. In the illustrated embodiment, the proximal end of one lead (or one lead extension) can be inserted into the lead connector 552. It will be recognized that the lead connector can be modified to receive any number of leads or lead extensions including, for example, one, two, three, four, or more leads or lead extensions. In FIG. 5B, the connector body 570 is made transparent to illustrate the interior mechanisms of the lead connector 552.

The lead connector 552 includes a connector body 570, a button 574, one or more side-loading apertures 577, one or more end apertures 579, one or more lead channels 580, and one or more stylet channels 582. Within the lead connector are one or more springs 576 (FIG. 5B), multiple connector contacts (not shown) arrayed along the one or more lead channels, and multiple conductors (not shown) that extend from the contacts to the elongated body. The button 574 includes an actuation surface 578, one or more button lead channels 581, a channel surface 584, and one or more lead retention members 586.

The one or more springs 576 bias the button 574 outward from the connector body 570, as illustrated in FIGS. 5A and 5B, which misaligns the one or more button lead channels 581 with the one or more lead channels 580. To load a lead into the lead connector, a user pushes the actuation surface 578 of the button 574 to depress the button so that the one or more button lead channels 581 align with the one or more lead channels 580. A lead can then be side-loaded (inserted laterally) through the side-loading aperture 577, or end-loaded (slid longitudinally, relative to the lead) through the end aperture 579, into the lead channel 580 and button lead channel 581. The lead can also include a stylet inserted within the lead. The stylet can be pulled out of the lead so that the stylet handle is spaced apart from the lead and then the stylet can be side-loaded (inserted laterally) into the stylet channel 582 (and, optionally, in part of the lead channel 580) as the lead is end-loaded or side-loaded into the lead channel 580. The junction 583 between the lead channel 580 and the stylet channel 582 can act as a lead stop. A practitioner can push the lead into the lead channel until the end of the lead reaches the junction 583. Using the junction 583 as a lead stop can also facilitate aligning the terminals on the lead with the connector contacts in the lead connector 552.

Once the lead is loaded into the lead channel 580 and button lead channel 581, the button 574 can be released which results in the button 574 moving outwardly with respect to the connector body 570 due to the biasing of the one or more springs 576. This movement again misaligns the one or more button lead channels 581 with the one or more lead channels 580 to engage and hold the lead within the lead connector 552. In at least some embodiments, the resulting misalignment creates a non-straight or tortuous pathway to resist removal of the lead. In at least some embodiments, the resulting misalignment forms a friction fit with, or compresses, portions of the lead within or adjacent to the button lead channel to resist removal of the lead. In some embodiments, the button 574 includes one or more lead retention members 586, such as the upper and lower lips illustrated in FIGS. 5A and 5B, which, when the button 574 is released, retain the lead within the button lead channel 582 rather than let the lead slip out of the button lead channel.

In some embodiments, the connector body 570 is formed of two or more pieces 570a, 570b that can be held together by fasteners 571 disposed within apertures 573. Examples of fasteners include, but are not limited to, screws, bolts, and the like. The conductors and connector contacts can be inserted between the two or more pieces (or in any other suitable arrangement) during assembly. The connector contacts can be any suitable contacts including, but not limited to, metal strips, c-shaped metal elements, pogo pins, or the like. In some embodiments, the connector body 570 can include an internal recess 587 and the button 574 can include a projection 588 that fits within the recess. The projection 588 can move up and down within the recess 587, but the recess 587 limits the upward and downward motion of the projection 588 (and thereby can limit the upward and downward motion of the button 574) to prevent the button 574 from disengagement with the connector body 570 when moving upward and limit the downward movement of the button so that the button lead channel 581 and the lead channel 580 align when the button is fully depressed.

Figure 6A:
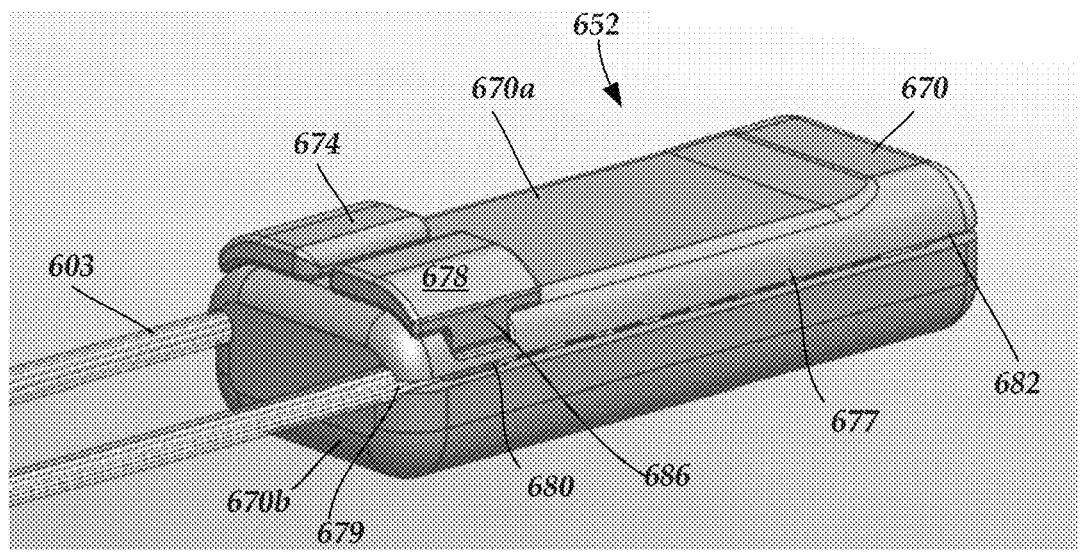
FIG. 6A is a schematic perspective view of a second embodiment of a lead connector of an operating room cable assembly, according to the invention.
Figure 6B:
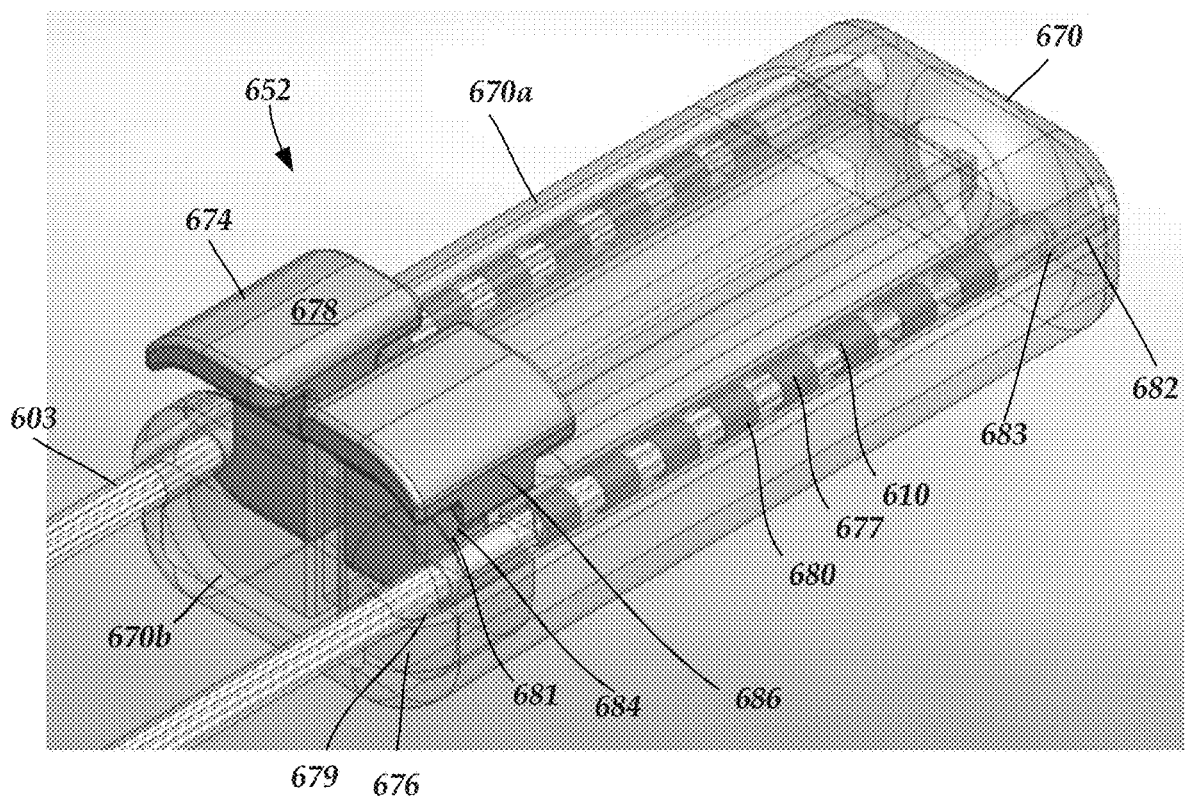
FIG. 6B is a schematic perspective view of the lead connector of FIG. 6A with the body made transparent for illustration purposes, according to the invention.

FIGS. 6A and 6B illustrate another embodiment of a lead connector 652 of an operating room cable assembly (such as operating room cable assembly 450 of FIG. 4) with an elongated body (not shown) extending from the lead connector. In the illustrated embodiment, the proximal end of two leads 603 (or two lead extensions or any combination thereof) can be inserted into the lead connector 652. It will be recognized that instead of using two leads or lead extensions, two lead bodies (see FIG. 2) can be inserted into the lead connector 652. It will be recognized that the lead connector can be modified to receive any number of leads or lead extensions including, for example, one, two, three, four, or more leads or lead extensions. In FIG. 6B, the connector body 670 is made transparent to illustrate the interior mechanisms of the lead connector 652. The lead connector 652 differs from the lead connector 552 in that it can receive two leads and has a separate button for each lead. In an alternative embodiment, the lead connector can receive two leads, but there is a single button that is depressed to load both leads.

The lead connector 652 includes a connector body 670, two buttons 674, two stylet side-loading apertures 677, two end apertures 679, two lead channels 680, and two stylet channels 682 (see FIG. 6B). Within the lead connector are two springs 676 (FIG. 6B), multiple connector contacts (not shown) arrayed along the one or more lead channels, and multiple conductors (not shown) that extend from the contacts to the elongated body. The buttons 674 each include an actuation surface 678, a button lead channel 681, a channel surface 684, and one or more lead retention members 686. In an alternative embodiment, the lead connector includes two side-loading apertures such as those illustrate in FIGS. 5A and 5B to allow side-loading of the leads into the lead channels. Similarly, the embodiment of FIGS. 5A and 5B can be modified to only allow end-loading of the lead as illustrated in FIGS. 6A and 6B.

The springs 676 bias the buttons 674 outward from the connector body 670, as illustrated in FIG. 6B, which misaligns the one or more button lead channels 681 with the one or more lead channels 680. To load a lead into the lead connector, a user pushes the actuation surface 678 of the corresponding button 674 to depress the button so that the selected button lead channel 681 aligns with the lead channel 680, as illustrated in FIG. 6A. A lead can then be end-loaded (slid longitudinally, relative to the lead) through the end aperture 679 into the lead channel 680 and button lead channel 681. The lead can also include a stylet inserted within the lead. The stylet can be pulled out of the lead so that the stylet handle is spaced apart from the lead and then the stylet can be side-loaded (inserted laterally) through the stylet side-loading aperture 677 into the stylet channel 682 and in part of the lead channel 680 as the lead is end-loaded into the lead channel 680. In alternative embodiments, the side-loading aperture can be similar to that illustrate in FIGS. 5A and 5B so that the lead can be side loaded into the lead channel. The junction 683 between the lead channel 680 and the stylet channel 682 can act as a lead stop. A practitioner can push the lead into the lead channel until the end of the lead reaches the junction 683. Using the junction 683 as a lead stop can also facilitate aligning the terminals 610 on the lead with the connector contacts in the lead connector 652.

Once the lead is loaded into the lead channel 680 and button lead channel 681, the button 674 can be released which results in the button 674 moving outwardly with respect to the connector body 670 due to the biasing of the spring 676. This movement again misaligns the button lead channel 681 with the lead channel 680 to engage and hold the lead within the lead connector 652. In at least some embodiments, the resulting misalignment creates a non-straight or tortuous pathway to resist removal of the lead. In at least some embodiments, the resulting misalignment forms a friction fit with, or compresses, portions of the lead within or adjacent to the button lead channel to resist removal of the lead. In some embodiments, the button 674 includes one or more lead retention members 686, such as the upper and lower lips illustrated in FIGS. 6A and 6B, which, when the button 674, is released retain the lead within the button lead channel 682 rather than let the lead slip out of the button lead channel. Because there are two buttons 674, each lead channel can be loaded separately with a different lead.

In some embodiments, the connector body 670 is formed of two or more pieces 670*a*, 670*b* that can be held together by fasteners. Examples of fasteners include, but are not limited to, screws, bolts, and the like. The conductors and connector contacts can be inserted between the two or more pieces (or in any other suitable arrangement) during assembly. The connector contacts can be any suitable contact including, but not limited to, metal strips, c-shaped metal elements, pogo pins, or the like. Optionally, each button can include a projection, similar to projection 588 described above, and the connector body can include one or two recess, similar to recess 587 described above, to restrict movement of the buttons.

Figure 7A:
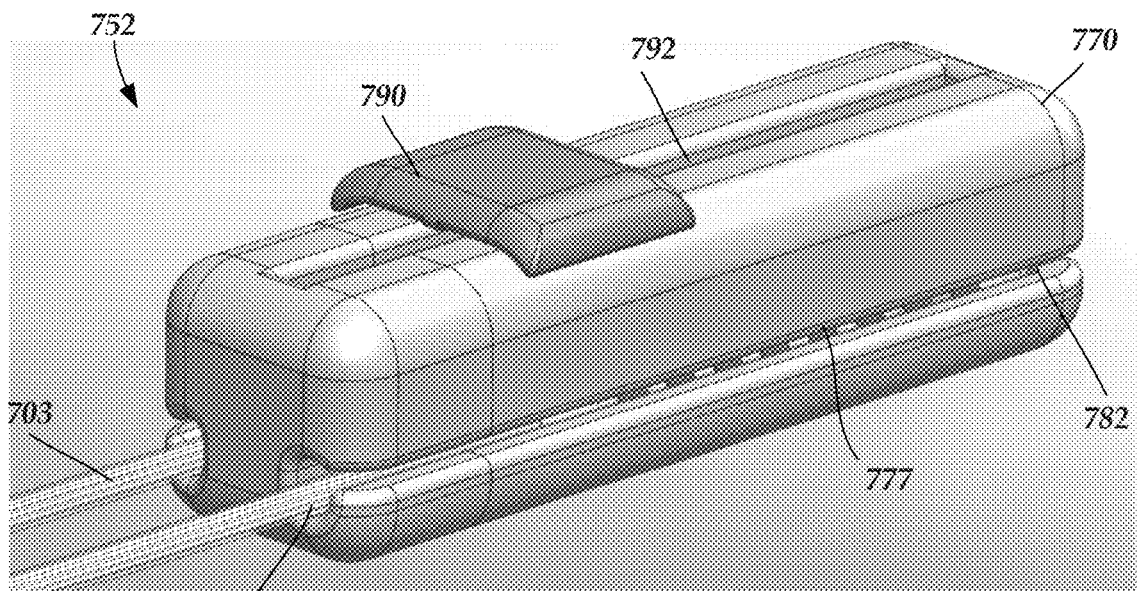
FIG. 7A is a schematic perspective view of a third embodiment of a lead connector of an operating room cable assembly, according to the invention.
Figure 7B:
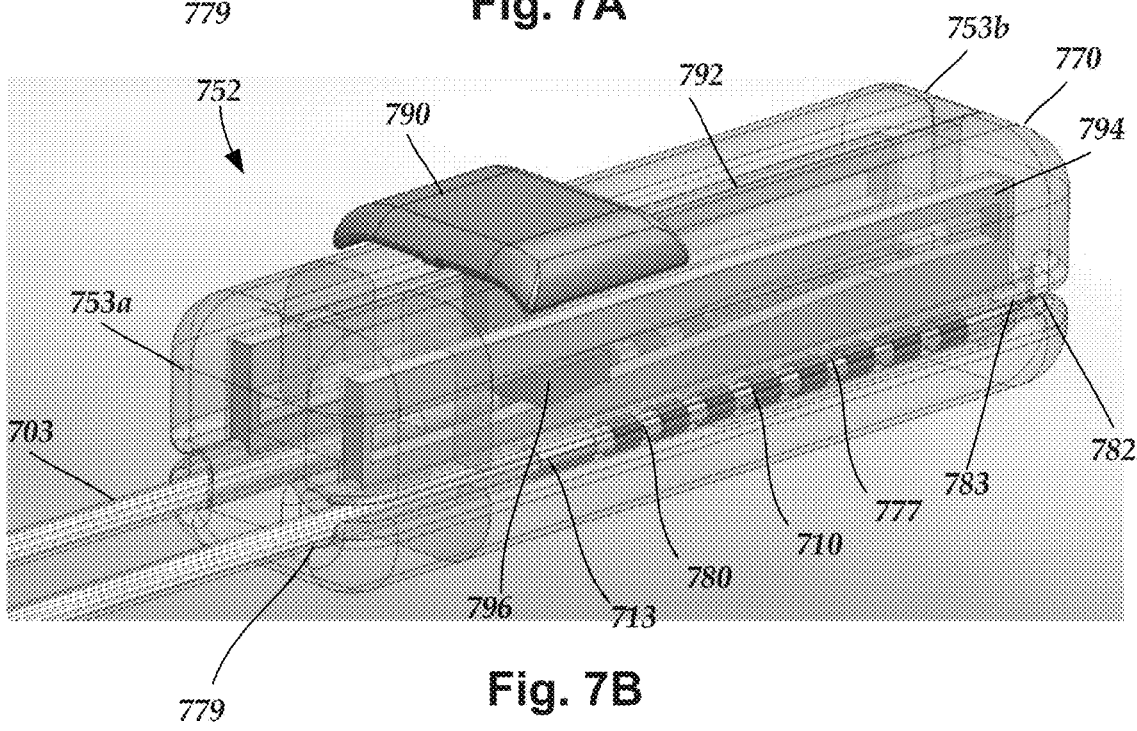
FIG. 7B is a schematic perspective view of the lead connector of FIG. 7A with the body made transparent for illustration purposes, according to the invention.

FIGS. 7A and 7B illustrate yet another embodiment of a lead connector 752 of an operating room cable assembly (such as operating room cable assembly 450 of FIG. 4) with an elongated body (not shown) extending from the lead connector. In the illustrated embodiment, the proximal end of two leads 703 (or two lead extensions or any combination thereof) can be inserted into the lead connector 752. It will be recognized that instead of using two leads or lead extensions, two lead bodies (see FIG. 2) can be inserted into the lead connector 752. It will be recognized that the lead connector can be modified to receive any number of leads or lead extensions including, for example, one, two, three, four, or more leads or lead extensions. In FIG. 7B, the connector body 770 is made transparent to illustrate the interior mechanisms of the lead connector 752. The lead connector 752 differs from the lead connector 552 in that it can receive two leads and has a slider to engage the leads and hold them within the lead connector. In an alternative embodiment, the lead connector can receive two leads and there is a separate slider for each lead.

The lead connector 752 includes a connector body 770, a slider 790, a slider aperture 792, two stylet side-loading apertures 777, two end apertures 779, two lead channels 780 (FIG. 7B), and two stylet channels 782. Within the lead connector are rails 794 (FIG. 7B), one or more lead engagement elements 796 (FIG. 7B), multiple connector contacts (not shown) arrayed along the one or more lead channels, and multiple conductors (not shown) that extend from the contacts to the elongated body. In an alternative embodiment, the lead connector includes two side-loading apertures such as those illustrate in FIGS. 5A and 5B to allow side-loading of the leads into the lead channels.

The one or more lead engagement element 796 are coupled to the slider 790 and ride along tracks in the rails 794, as illustrated in FIG. 7B. The tracks in the rails slope upwards from at, or near, one end 753*a* of the lead connector 752 to at, or near, the opposite end 753*b*. It will be understood that the slope of the tracks can be opposite to that illustrated and that operation of the device will be corresponding inverted. In the illustrated embodiment, when the slider 790 is near the opposite end 753*b*, the one or more lead engagement elements 796 are lifted away from the leads 703 and lead channels 780 so that the leads can be loaded into the lead connector 752. When the slider 790 is near the end 753*a* with the end apertures 779, as illustrated in FIGS. 7A and 7B, the one or more lead engagement elements 796 will engage any lead 703 within the lead channel 780 and hold it within the lead connector 752.

To load a lead 703 into the lead connector, a user pushes the slider 790 towards the end 753*b*. The lead can then be end-loaded (slid longitudinally, relative to the lead) through the end aperture 779 into the lead channel 780. The lead can also include a stylet inserted within the lead. The stylet can be pulled out of the lead so that the stylet handle is spaced apart from the lead and then the stylet can be side-loaded (inserted laterally) through the stylet side-loading aperture 777 into the stylet channel 782 and in part of the lead channel 780 as the lead is end-loaded into the lead channel 780. In alternative embodiments, the side-loading aperture can be similar to that illustrate in FIGS. 5A and 5B so that the lead can be side loaded into the lead channel. The junction 783 between the lead channel 780 and the stylet channel 782 can act as a lead stop. A practitioner can push the lead into the lead channel until the end of the lead reaches the junction 783. Using the junction 783 as a lead stop can also facilitate aligning the terminals 710 on the lead with the connector contacts in the lead connector 752.

Once the lead is loaded into the lead channel 780, the slider 790 is pushed back toward the end 753*a*. This causes the one or more lead engagement elements 796 ride along the tracks in the rails 794 until the one or more lead engagement elements engage the lead 703. The engagement can be, for example, a friction or compression fit between the lead engagement element and the lead. In some embodiments, the lead 703 may include a metal or hard plastic retainer sleeve 713 which the lead engagement element 796 may contact to avoid or reduce any damage to the lead.

Figure 7C:
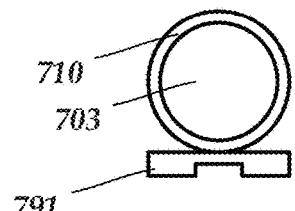
FIG. 7C is a schematic cross-sectional view of a lead interacting with a connector contact of the lead connector of FIG. 7A prior to engaging the lead with the lead engagement element, according to the invention.
Figure 7D:
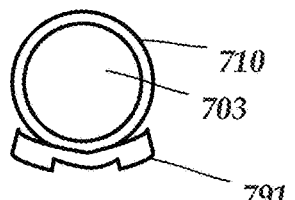
FIG. 7D is a schematic cross-sectional view of a lead interacting with a connector contact of the lead connector of FIG. 7A after engaging the lead with the lead engagement element, according to the invention.

In some embodiments, the connector body 770 is formed of two or more pieces that can be held together by fasteners. Examples of fasteners include, but are not limited to, screws, bolts, and the like. The conductors and connector contacts can be inserted between the two or more pieces (or in any other suitable arrangement) during assembly. The connector contacts can be any suitable contact including, but not limited to, metal strips, c-shaped metal elements, pogo pins, or the like. In some embodiments, as illustrated in FIGS. 7C and 7D, the connector contacts 791 are metal plates, optionally with material removed from the middle of the plate, disposed at the bottom, side, or top of the lead channel 780 upon which the lead 703 can sit or otherwise contact, as illustrated in FIG. 7C. When the lead engagement element pushes against the lead 703, the connector contacts 791 are deformed to create a better electrical contact with the terminals 710 of the lead 703, as illustrated in FIG. 7D.

Figure 8:
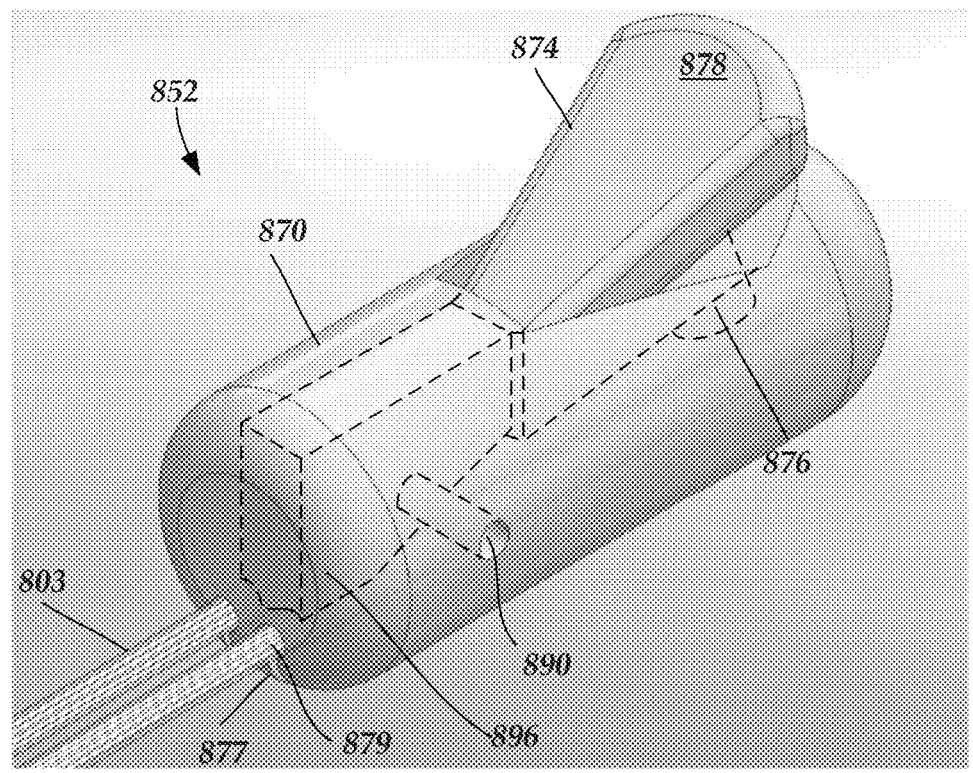
FIG. 8 is a schematic perspective view of a fourth embodiment of a lead connector of an operating room cable assembly, according to the invention.

FIG. 8 illustrates a further embodiment of a lead connector 852 of an operating room cable assembly (such as operating room cable assembly 450 of FIG. 4) with an elongated body (not shown) extending from the lead connector. In the illustrated embodiment, the proximal end of two leads 803 (or two lead extensions or any combination thereof) can be inserted into the lead connector 852. It will be recognized that instead of using two leads or lead extensions, two lead bodies (see FIG. 2) can be inserted into the lead connector 852. It will be recognized that the lead connector can be modified to receive any number of leads or lead extensions including, for example, one, two, three, four, or more leads or lead extensions.

The lead connector 852 includes a connector body 870, a lever 874, an actuation surface 878, two stylet side-loading apertures 877 (which are open underneath the connector body 870 in the illustrated embodiment), two end apertures 879, two lead channels (not shown, but similar to the lead channels in the preceding embodiments), and two stylet channels (not shown, but similar to the stylet channels in the preceding embodiments). Within the lead connector is a cantilever bar 890, a spring 876, a lead engagement element 896, multiple connector contacts (not shown) arrayed along the one or more lead channels, and multiple conductors (not shown) that extend from the contacts to the elongated body.

The spring 876 biases the actuation surface 878 of the lever 874 outward from the connector body 870, as illustrated in FIG. 8, and pushes the lead engagement element 896 against any lead 803 within the lead channels. To load a lead into the lead connector, a user pushes the actuation surface 878 of the corresponding lever 874 to depress the lever so that the lead engagement element 896 is lifted (using the cantilever bar 890) away from the lead channels. A lead can then be end-loaded (slid longitudinally, relative to the lead) through the end aperture 879 into the lead channel. The lead can also include a stylet inserted within the lead. The stylet can be pulled out of the lead so that the stylet handle is spaced apart from the lead and then the stylet can be side-loaded (inserted laterally) through the stylet side-loading aperture 877 into the stylet channel 882 and in part of the lead channel as the lead is end-loaded into the lead channel. A junction (not shown but similar to the junctions described in the previous embodiments) between the lead channel and the stylet channel can act as a lead stop. A practitioner can push the lead into the lead channel until the end of the lead reaches the junction. Using the junction as a lead stop can also facilitate aligning the terminals on the lead with the connector contacts in the lead connector 852.

Once the lead is loaded into the lead channel 880, the lever 874 can be released which results in the lever 874 moving outwardly with respect to the connector body 870 due to the biasing of the spring 876. This movement causes the lead engagement element 896 to engage the leads 803 within the lead channels.

In some embodiments, the connector body 870 is formed of two or more pieces that can be held together by fasteners. Examples of fasteners include, but are not limited to, screws, bolts, and the like. The conductors and connector contacts can be inserted between the two or more pieces (or in any other suitable arrangement) during assembly. The connector contacts can be any suitable contact including, but not limited to, metal strips, c-shaped metal elements, pogo pins, or the like.

Figure 9:
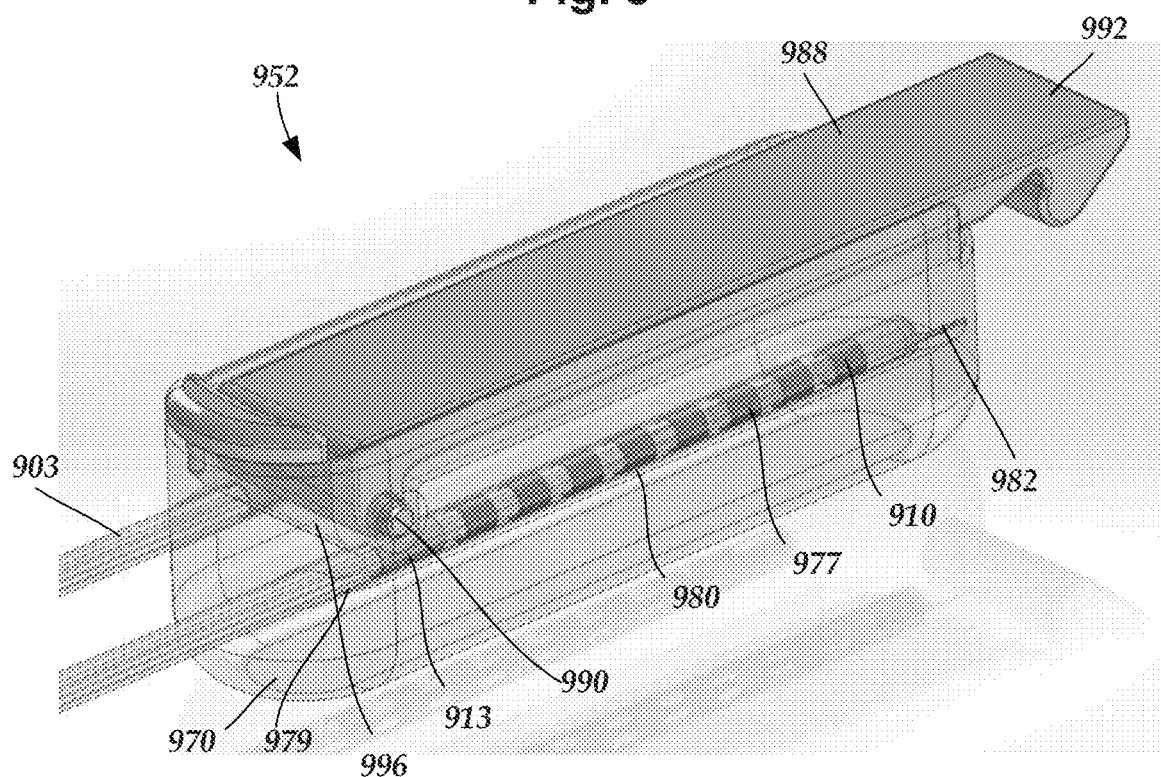
FIG. 9 is a schematic perspective view of a fifth embodiment of a lead connector of an operating room cable assembly, according to the invention.

FIG. 9 illustrates another embodiment of a lead connector 952 of an operating room cable assembly (such as operating room cable assembly 450 of FIG. 4) with an elongated body (not shown) extending from the lead connector. In the illustrated embodiment, the proximal end of two leads 903 (or two lead extensions or any combination thereof) can be inserted into the lead connector 952. It will be recognized that instead of using two leads or lead extensions, two lead bodies (see FIG. 2) can be inserted into the lead connector 952. It will be recognized that the lead connector can be modified to receive any number of leads or lead extensions including, for example, one, two, three, four, or more leads or lead extensions.

The lead connector 952 includes a connector body 970, a lever 988, a lever handle 992, two stylet side-loading apertures 977, two end apertures 979, two lead channels 980, and two stylet channels 982. Within the lead connector is a cantilever bar 990, a lead engagement element 996, multiple connector contacts (not shown) arrayed along the one or more lead channels, and multiple conductors (not shown) that extend from the contacts to the elongated body. In an alternative embodiment, the lead connector includes two side-loading apertures such as those illustrate in FIGS. 5A and 5B to allow side-loading of the leads into the lead channels.

When the lever 988 is down, as illustrated in FIG. 9, the lead engagement element 996 pushes against any lead 903 within the lead channels 980 and may form a friction or compression fit with the leads. To load a lead into the lead connector, a user pulls up on the lever 988 so that the lead engagement element 996 is lifted (using the cantilever bar 990) away from the lead channels. A lead can then be end-loaded (slid longitudinally, relative to the lead) through the end aperture 979 into the lead channel. The lead can also include a stylet inserted within the lead. The stylet can be pulled out of the lead so that the stylet handle is spaced apart from the lead and then the stylet can be side-loaded (inserted laterally) through the stylet side-loading aperture 977 into the stylet channel 982 and in part of the lead channel as the lead is end-loaded into the lead channel. A junction (not shown but similar to the junctions described in the previous embodiments) between the lead channel and the stylet channel can act as a lead stop. A practitioner can push the lead into the lead channel until the end of the lead reaches the junction. Using the junction as a lead stop can also facilitate aligning the terminals 910 on the lead with the connector contacts in the lead connector 952.

Once the lead is loaded into the lead channel 980, the lever 988 is pushed down which causes the lead engagement element 996 to engage the leads 903 with the lead channels. In some embodiments, the lead 903 may include a metal or hard plastic retainer sleeve 913 which the lead engagement element 996 may press to avoid or reduce any damage to the lead. In some embodiments, the lead connector 952 includes a locking mechanism to lock the lever 988 in the down position, as illustrated in FIG. 9, until a user pulls the handle 992 upwards to disengage the locking mechanism. Any suitable locking mechanism can be used including, for example, a lip and detent in the connector body 970 to receive and hold a portion of the lever 988.

In some embodiments, the connector body 970 is formed of two or more pieces that can be held together by fasteners. Examples of fasteners include, but are not limited to, screws, bolts, and the like. The conductors and connector contacts can be inserted between the two or more pieces (or in any other suitable arrangement) during assembly. The connector contacts can be any suitable contact including, but not limited to, metal strips, c-shaped metal elements, pogo pins, or the like.

Figure 10:
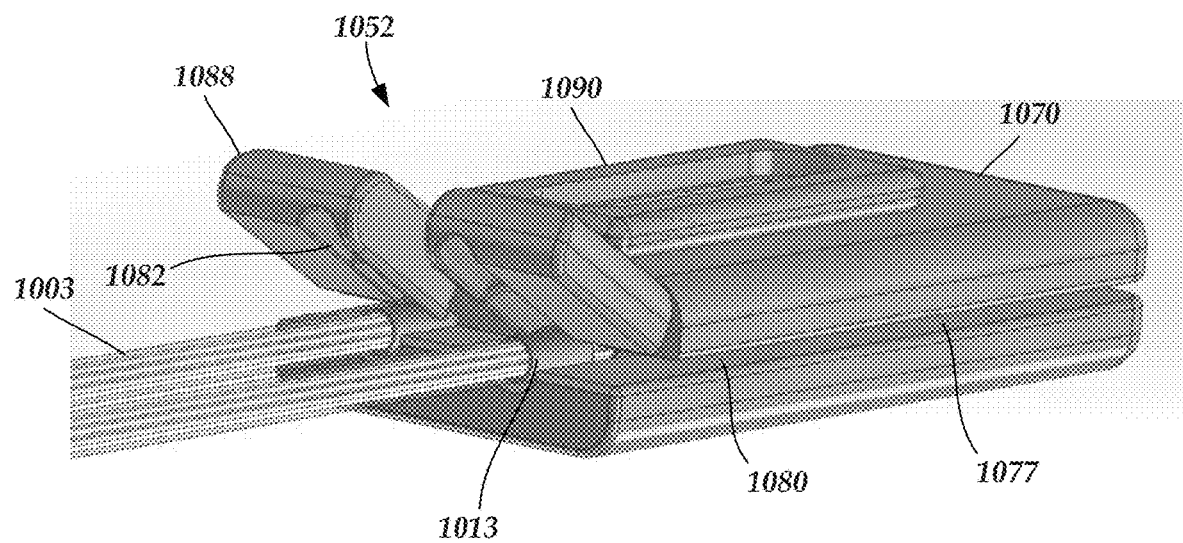
FIG. 10 is a schematic perspective view of a sixth embodiment of a lead connector of an operating room cable assembly, according to the invention.

FIG. 10 illustrates yet another embodiment of a lead connector 1052 of an operating room cable assembly (such as operating room cable assembly 450 of FIG. 4) with an elongated body (not shown) extending from the lead connector. In the illustrated embodiment, the proximal end of two leads 1003 (or two lead extensions or any combination thereof) can be inserted into the lead connector 1052. It will be recognized that instead of using two leads or lead extensions, two lead bodies (see FIG. 2) can be inserted into the lead connector 1052. It will be recognized that the lead connector can be modified to receive any number of leads or lead extensions including, for example, one, two, three, four, or more leads or lead extensions.

The lead connector 1052 includes a connector body 1070, two doors 1088, a locking slider 1090 two stylet side-loading apertures 1077, two lead channels 1080, two door channels 1082 and two stylet channels (not shown, but similar to the stylet channels in the preceding embodiments). Within the lead connector are multiple connector contacts (not shown) arrayed along the lead channels and multiple conductors (not shown) that extend from the contacts to the elongated body. The doors 1088 are attached to the connector body 1070 so that the doors can swing between a closed position and an open position. The doors 1088 can be attached in any suitable manner including, but not limited to, a hinged arrangement.

When the doors 1088 are closed, the door channels 1082 hold the lead 1003 within the lead connector 1052. In at least some embodiments, the door channels (and optionally portions of the lead channels 1080 opposite the door channels) are smaller (or equal) in diameter than the lead 1003 or an optional retaining sleeve 1013, or include one or protrusions, to engage and hold the lead or the optional retaining sleeve when the door 1088 is closed. To load a lead into the lead connector, a user opens one of the doors 1088, as illustrated in FIG. 10, so that the lead channel 1080 is accessible. A lead can then be end-loaded (slid longitudinally, relative to the lead) into the lead channel 1080. The lead can also include a stylet inserted within the lead. The stylet can be pulled out of the lead so that the stylet handle is spaced apart from the lead and then the stylet can be side-loaded (inserted laterally) through the stylet side-loading aperture 1077 into the stylet channel 1082 and in part of the lead channel as the lead is end-loaded into the lead channel. A junction (not shown but similar to the junctions described in the previous embodiments) between the lead channel and the stylet channel can act as a lead stop. A practitioner can push the lead into the lead channel until the end of the lead reaches the junction. Using the junction as a lead stop can also facilitate aligning the terminals on the lead with the connector contacts in the lead connector 1052.

Once the lead is loaded into the lead channel 1080, the door 1088 is closed to engage the lead 1003 with the lead channel 1080 and door channel 1082. In at least some embodiments, the lead connector 1052 includes locking slider 1090 that can be slid over at least a portion of the doors 1088 to lock the doors in the closed position. Alternatively, any other suitable locking mechanism can be used to hold the doors in the closed position.

In some embodiments, the connector body 1070 is formed of two or more pieces that can be held together by fasteners. Examples of fasteners include, but are not limited to, screws, bolts, and the like. The conductors and connector contacts can be inserted between the two or more pieces (or in any other suitable arrangement) during assembly. The connector contacts can be any suitable contact including, but not limited to, metal strips, c-shaped metal elements, pogo pins, or the like.

Figure 11:
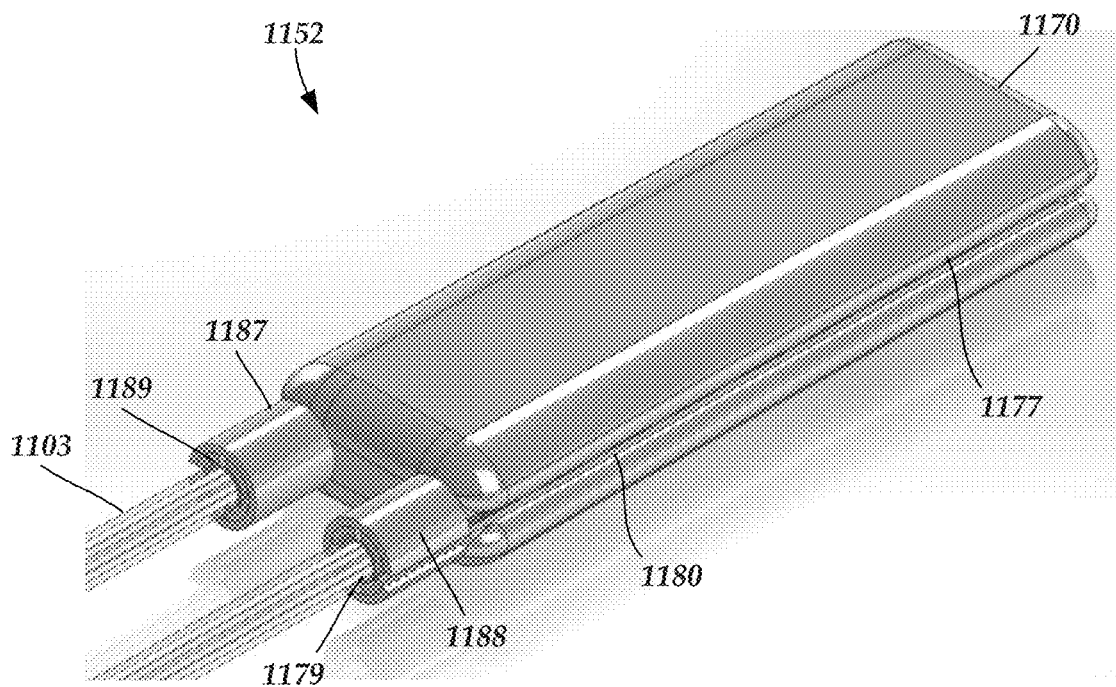
FIG. 11 is a schematic perspective view of a seventh embodiment of a lead connector of an operating room cable assembly, according to the invention.

FIG. 11 illustrates a further embodiment of a lead connector 1152 of an operating room cable assembly (such as operating room cable assembly 450 of FIG. 4) with an elongated body (not shown) extending from the lead connector. In the illustrated embodiment, the proximal end of two leads 1103 (or two lead extensions or any combination thereof) can be inserted into the lead connector 1152. It will be recognized that instead of using two leads or lead extensions, two lead bodies (see FIG. 2) can be inserted into the lead connector 1152. It will be recognized that the lead connector can be modified to receive any number of leads or lead extensions including, for example, one, two, three, four, or more leads or lead extensions.

The lead connector 1152 includes a connector body 1170, two lead retainers 1188 extending from the connector body, two stylet side-loading apertures 1177, two end apertures 1179, two lead channels 1180, and two stylet channels (not shown, but similar to the stylet channels in the preceding embodiments). Within the lead connector are multiple connector contacts (not shown) arrayed along the one or more lead channels and multiple conductors (not shown) that extend from the contacts to the elongated body.

The lead retainers 1188 include a threaded collet 1189 and a threaded sleeve 1187 disposed around the collet. The sleeve 1187 can be rotated to increase or decrease the inner diameter of the collet 1189. In alternative embodiments, the inner diameter of the collet can be increased or decreased by pushing or pulling the sleeve.

To load a lead into the lead connector, a user rotates the sleeve 1187 to open the collet 1189 sufficiently to receive the lead. A lead can then be end-loaded (slid longitudinally, relative to the lead) through the end aperture 1179 into the lead channel. The lead can also include a stylet inserted within the lead. The stylet can be pulled out of the lead so that the stylet handle is spaced apart from the lead and then the stylet can be side-loaded (inserted laterally) through the stylet side-loading aperture 1177 into the stylet channel and in part of the lead channel as the lead is end-loaded into the lead channel. A junction (not shown but similar to the junctions described in the previous embodiments) between the lead channel and the stylet channel can act as a lead stop. A practitioner can push the lead into the lead channel until the end of the lead reaches the junction. Using the junction as a lead stop can also facilitate aligning the terminals 1110 on the lead with the connector contacts in the lead connector 1152.

Once the lead is loaded into the lead channel 1180, the sleeve 1187 is rotated to reduce the inner diameter of the collet 1189 so that the collet grips the lead 1103 or, optionally, a retaining sleeve on the lead. The lead 1103 can be released by rotating the sleeve 1187 to loosen the collet 1189 from around the lead.

In some embodiments, the connector body 1170 is formed of two or more pieces that can be held together by fasteners. Examples of fasteners include, but are not limited to, screws, bolts, and the like. The conductors and connector contacts can be inserted between the two or more pieces (or in any other suitable arrangement) during assembly. The connector contacts can be any suitable contact including, but not limited to, metal strips, c-shaped metal elements, pogo pins, or the like.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An operating room cable assembly for electrically coupling an electrical stimulation lead to a trial stimulator, the operating room cable assembly comprising:
   an elongated body having a first end portion and an opposing second end portion;
   a lead connector disposed along the first end portion of the elongated body, the lead connector configured and arranged to mechanically receive a proximal end portion of a first electrical stimulation lead or lead extension, the lead connector comprising
      a connector body defining at least a first portion of a first lead channel,
      a first button defining at least a second portion of the first lead channel, wherein the first lead channel is configured and arranged to receive a portion of the first electrical stimulation lead or lead extension, a first spring disposed within the connector body, the first spring biasing the first button to a lead holding position, wherein the first button is configured to be pushed to a lead loading position so that the portion of the first electrical stimulation lead or lead extension can be loaded into the first lead channel and, when the first button is released, the first spring biases the first button to the lead holding position to engage and hold the portion of the first electrical stimulation lead or lead extension within the lead connector, a plurality of first connector contacts disposed within the connector body and arranged along the first lead channel and configured and arranged to make electrical contact with terminals disposed on the portion of the first electrical stimulation lead or lead extension when the portion of the first electrical stimulation lead or lead extension is received in the first lead channel.

2. The operating room cable assembly of claim 1, wherein the first button comprises an actuation surface and a channel surface, wherein the second portion of the first lead channel is disposed between the actuation surface and the channel surface of the first button.

3. The operating room cable assembly of claim 1, wherein the lead connector further defines a first stylet channel associated with, and extending from, the first lead channel, wherein the first stylet channel has an outer diameter smaller than an outer diameter of the first lead channel.

4. The operating room cable assembly of claim 3, wherein the lead connector further defines a first side-loading stylet aperture associated with the first stylet channel and sufficiently sized so that a portion of a stylet extending out of the first electrical stimulation lead or lead extension can be laterally loaded into the first stylet channel.

5. The operating room cable assembly of claim 3, wherein a junction between the first lead channel and the first stylet channel forms a lead stop to prevent further insertion of the portion of the first electrical stimulation lead or lead extension beyond the junction.

6. The operating room cable assembly of claim 1, wherein the lead connector further comprises a first side-loading lead aperture associated with the first lead channel and sufficiently sized so that the portion of the first electrical stimulation lead or lead extension can be laterally loaded into the first lead channel.

7. The operating room cable assembly of claim 1, wherein the connector body further defines a recess and the first button comprises a protrusion, wherein the recess and protrusion are configured and arranged to limit upward or downward movement of the first button.

8. The operating room cable assembly of claim 1, wherein the lead connector further comprises at least one lead retention element associated with the first lead channel to facilitate retention of the portion of the first electrical stimulation lead or lead extension within the first lead channel.

9. The operating room cable assembly of claim 8, wherein the at least one lead retention element is coupled to the first button and moves with the first button.

10. The operating room cable assembly of claim 1, wherein the lead connector is further configured and arranged to mechanically receive a proximal end portion of a second electrical stimulation lead or lead extension, wherein the lead connector further comprises
a second lead channel, wherein a first portion of the second lead channel is defined within the connector body and a second portion of the second lead channel is defined by the first button, wherein the second lead channel is configured and arranged to receive a portion of the second electrical stimulation lead or lead extension, and
a plurality of second connector contacts disposed within the connector body and arranged along the second lead channel and configured and arranged to make electrical contact with terminals disposed on the portion of the second electrical stimulation lead or lead extension when the portion of the second electrical stimulation lead or lead extension is received in the second lead channel.

11. The operating room cable assembly of claim 10, wherein the lead connector further defines a second stylet channel associated with, and extending from, the second lead channel, wherein the second stylet channel has an outer diameter smaller than an outer diameter of the second lead channel.

12. The operating room cable assembly of claim 1, wherein the lead connector is further configured and arranged to mechanically receive a proximal end portion of a second electrical stimulation lead or lead extension, wherein the lead connector further comprises
a second button,
a second lead channel, wherein a first portion of the second lead channel is defined within the connector body and a second portion of the second lead channel is defined by the second button, wherein the second lead channel is configured and arranged to receive a portion of the second electrical stimulation lead or lead extension
a second spring disposed within the connector body, the second spring biasing the second button to a lead holding position, wherein the second button is configured to be pushed to a lead loading position so that the portion of the second electrical stimulation lead or lead extension can be loaded into the second lead channel and, when the second button is released, the second spring biases the second button to the lead holding position to engage and hold the portion of the second electrical stimulation lead or lead extension within the lead connector, and
a plurality of second connector contacts disposed within the connector body and arranged along the second lead channel and configured and arranged to make electrical contact with terminals disposed on the portion of the second electrical stimulation lead or lead extension when the portion of the second electrical stimulation lead or lead extension is received in the second lead channel.

13. The operating room cable assembly of claim 1, further comprising a trial stimulator connector disposed along the second end portion of the elongated body and electrically coupled to the lead connector.

14. The operating room cable assembly of claim 1, further comprising a plurality of the first springs.

15. A method of using the operating room cable assembly of claim 1, the method comprising
pushing the first button to the lead loading position;
inserting the portion of the first electrical stimulation lead or lead extension into the first lead channel; and
releasing the first button, wherein the first spring returns the first button to the lead holding position with the first button engaging and holding the portion of the first electrical stimulation lead or lead extension within the lead connector.

16. A kit comprising:

the operating room cable assembly of claim 1; and an electrical stimulation lead having a distal end portion and a proximal end portion and comprising a plurality of electrodes disposed along the distal end portion of the electrical stimulation lead, a plurality of terminals disposed along the proximal end portion of the electrical stimulation lead, and a plurality of conductors coupling the plurality of electrodes to the plurality of terminals, wherein the proximal end portion of the electrical stimulation lead is insertable into the lead connector of the operating room cable assembly.

17. The kit of claim 16, further comprising a lead extension having a distal end portion and a proximal end portion and comprising a connector disposed on the distal end portion of the lead extension to receive the proximal end portion of the electrical stimulation lead, a plurality of terminals disposed along the proximal end portion of the lead extension, and a plurality of conductors electrically coupling the connector to the plurality of terminals of the lead extension, wherein the proximal end portion of the lead extension is insertable into the lead connector of the operating room cable assembly.

18. A trial stimulation arrangement for an electrical stimulation system, the trial stimulation arrangement comprising:

the kit of claim 16; and a trial stimulator configured and arranged to generate electrical stimulation signals, the trial stimulator disposed external to a patient and coupleable to the operating room cable assembly of the kit.

19. A kit comprising:

the operating room cable assembly of claim 1; and a lead extension having a distal end portion and a proximal end portion and comprising a connector disposed on the distal end portion of the lead extension to receive the proximal end portion of an electrical stimulation lead, a plurality of terminals disposed along the proximal end portion of the lead extension, and a plurality of conductors electrically coupling the connector to the plurality of terminals of the lead extension, wherein the proximal end portion of the lead extension is insertable into the lead connector of the operating room cable assembly.

20. A trial stimulation arrangement for an electrical stimulation system, the trial stimulation arrangement comprising:

the kit of claim 19; and a trial stimulator configured and arranged to generate electrical stimulation signals, the trial stimulator disposed external to a patient and coupleable to the operating room cable assembly of the kit.

* * * * *